(12) United States Patent
Filho et al.

(10) Patent No.: US 6,613,281 B2
(45) Date of Patent: Sep. 2, 2003

(54) INTEGRATED HEAT EXCHANGER/RESERVOIR

(75) Inventors: José D'Elia Filho, Sao Paulo (BR); José Francisco Biscegli, Sao Paulo (BR)

(73) Assignee: Edwards Lifesciences Corporation, Irvine, CA (US)

( * ) Notice: Subject to any disclaimer, the term of this patent is extended or adjusted under 35 U.S.C. 154(b) by 0 days.

(21) Appl. No.: 09/843,581

(22) Filed: Apr. 26, 2001

(65) Prior Publication Data

US 2001/0033813 A1 Oct. 25, 2001

Related U.S. Application Data

(62) Division of application No. 09/075,409, filed on May 8, 1998, now abandoned.

(51) Int. Cl.[7] .......... A61M 1/14; A61M 37/00; F02C 3/06; B01D 63/00
(52) U.S. Cl. .......... 422/46; 422/44; 604/4.01; 604/6.13; 604/6.15; 261/158; 261/DIG. 28; 165/163; 210/321.79
(58) Field of Search .......... 604/4.01, 5.01, 604/6.01, 6.09, 6.11, 6.13, 6.15; 422/44, 46; 210/645, 650, 175, 176, 184, 186, 188, 180, 294–95, 321.6, 321.64, 321.72–321.78, 348, 349, 321.79, 321.8, 32.87; 261/158–159, DIG. 28; 165/58, 104.11, 104.19, 104.21, 104.27, 177, 163, 180–184, DIG. 355, DIG. 525

(56) References Cited

U.S. PATENT DOCUMENTS

| | | | |
|---|---|---|---|
| 4,138,288 A | * | 2/1979 | Lewin .......... 128/DIG. 3 |
| 4,289,623 A | | 9/1981 | Lee |
| 4,424,190 A | | 1/1984 | Mather, III et al. |
| 4,656,645 A | | 4/1987 | Martinez et al. |
| 4,818,490 A | | 4/1989 | Carson et al. |
| 4,874,581 A | * | 10/1989 | Sutherland et al. .... 128/DIG. 3 |
| 4,876,066 A | * | 10/1989 | Bringham et al. ..... 128/DIG. 3 |
| 4,975,247 A | | 12/1990 | Badolato et al. |
| 5,039,482 A | * | 8/1991 | Panzani et al. ........ 128/DIG. 3 |
| 5,043,140 A | * | 8/1991 | Combs .......... 128/DIG. 3 |
| 5,236,586 A | | 8/1993 | Antoni et al. |
| 5,240,677 A | | 8/1993 | Jones et al. |
| 5,297,591 A | | 3/1994 | Baurmeister |
| 5,316,724 A | | 5/1994 | Mathewson et al. |
| 5,346,621 A | | 9/1994 | Haworth et al. |
| 5,376,334 A | | 12/1994 | Haworth et al. |
| 5,733,398 A | * | 3/1998 | Carson et al. .......... 156/69 |
| 5,823,987 A | | 10/1998 | Elgas et al. |
| 5,964,725 A | | 10/1999 | Sato et al. |
| 6,004,511 A | | 12/1999 | Biscegli |
| 6,117,390 A | * | 9/2000 | Corey, Jr. .......... 422/44 |

FOREIGN PATENT DOCUMENTS

| | | |
|---|---|---|
| EP | 0 507 772 A1 | 10/1992 |
| WO | 97/08933 | 3/1997 |

* cited by examiner

*Primary Examiner*—Angela D. Sykes
*Assistant Examiner*—Patricia Bianco
(74) *Attorney, Agent, or Firm*—John Christopher James; Guy L. Cumberbatch

(57) ABSTRACT

An integrated heat exchanger/reservoir for use alone or in combination in an extracorporeal blood circuit. The reservoir includes a hard outer shell topped by a lid with a venous blood inlet. Blood from the inlet enters an elongated annular heat exchange chamber defined between two vertical cylindrical walls within the reservoir. A plurality of heat exchange coils in the annular chamber provides an efficient heat transfer function with low prime volume requirement. Cardiotomy fluid may be first debubbled and then combined with the venous blood stream entering the heat exchange chamber. After passing through the heat exchange chamber, the blood passes through a series of filters before being pumped to the oxygenator.

8 Claims, 9 Drawing Sheets

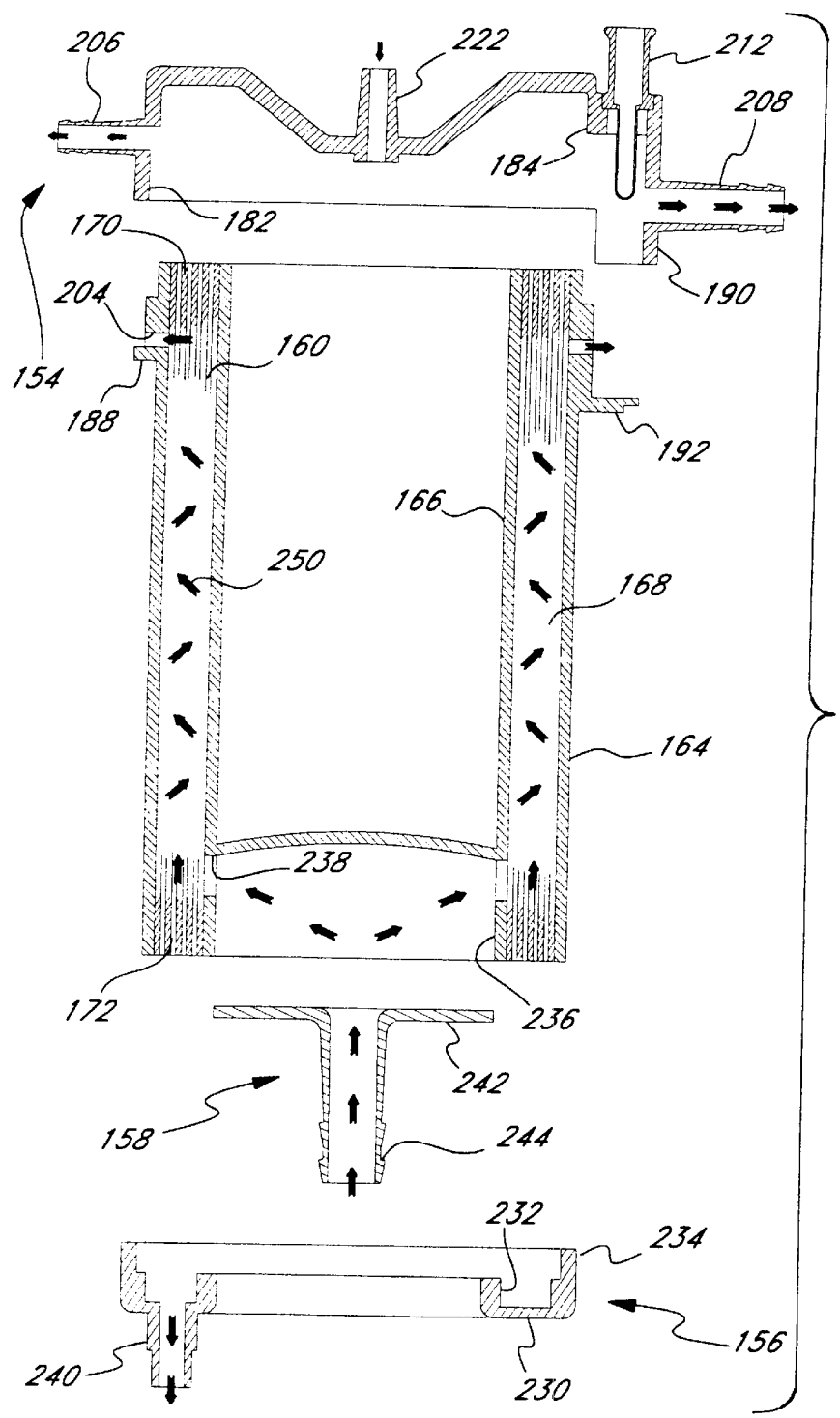

US 6,613,281 B2

INTEGRATED HEAT EXCHANGER/RESERVOIR

RELATED APPLICATION

The present application is a divisional of application Ser. No. 09/075,409, filed May 8, 1998 now abandoned.

FIELD OF THE INVENTION

The present invention relates generally to extracorporeal fluid circuits and, more particularly, to a compact membrane oxygenator and combined reservoir/heat exchanger used alone or in conjunction to reduce the prime volume of an extracorporeal blood circuit.

BACKGROUND OF THE INVENTION

Cardiopulmonary bypass (CPB) surgery requires a perfusion system, or extracorporeal oxygenation circuit, to maintain an adequate supply of oxygen in the patient's blood during the surgery. A venous return cannula inserted in one of the veins leading directly to the heart receives the "used" blood for rejuvenation through the perfusion system. The blood flows out of the patient into an extracorporeal fluid circuit having a conduit (typically a transparent flexible tube) to a venous reservoir that may also receive fluid from cardiotomy suckers. Commonly, one or more suckers extracts excess fluid from the chest cavity during the operation and diverts the fluid, which may contain bone chips or other particulates, into the top of the reservoir.

Typically, a centrifugal or roller pump impels blood, for example, from the venous/cardiotomy reservoir through a blood oxygenator and back to the patient. The pump assumes the pumping task of the heart and perfuses the patient's circulatory system. The oxygenator directs a flow of blood across a semi-permeable membrane or a plurality of semi-permeable fibers to transfer oxygen to and carbon dioxide from the blood. The oxygenator often incorporates a heat exchange system to regulate the extracorporeal blood temperature, termed a "closed" system. Before reaching the patient, the blood may pass through a temperature control monitoring system and along a conduit through an arterial filter and bubble detector, before reaching an arterial cannula positioned in a main artery of the patient.

The various components such as the reservoir, oxygenator and arterial filter require a minimum volume of blood to begin circulation. All of the components taken together require a "prime" volume of blood defined as that volume of blood outside the patient, or extracorporeal. The term "prime volume" can also be used to specify the volumetric capacity of each extracorporeal component in the system.

There are number of performance measurements for oxygenators. Important considerations include gas transfer capabilities, priming volume, blood compatibility, sterility, assembly, and maintenance. Effective oxygenators provided sufficient gas transfer with a minimum pressure drop and prime volume. In addition, the flow capacity through the oxygenator must be sufficient for the particular patient. Often, there is a trade-off in one or more of these performance characteristics to obtain a low priming volume or high flow rate, for example.

The need for a large prime volume in an extracorporeal fluid circuit is contrary to the best interest of the patient who is undergoing the surgery and is in need of the maximum possible amount of fully oxygenated blood. This is especially true of smaller adults, children, and pediatric or infant patients. Therefore, a significant amount of research and development has been directed toward reducing the prime volume within CPB systems. One area in which such a reduction of volume can be attained is to reduce the volume of the individual components, such as the reservoir, or blood oxygenator. There are limits to how small these components can be made, however, such as a need for adequate oxygen transfer to the blood, which depends in part on a sufficient blood/membrane interface area.

Much of the development in recent years has been toward reducing the prime volume of oxygenators while maintaining adequate flow rate and gas transfer capabilities. Unfortunately, this is not an easily attainable goal, and many of the smallest prime volume oxygenators have such a reduced flow rate that they are only useful for neonatal or infant patients, or exhibit some other performance disadvantage. Conversely, many oxygenators which otherwise have adequate performance, require a higher priming volume. For example, most of the most widely used commercial membrane oxygenators on the market for adult patients have priming volumes of between 0.3 and 0.6 liters. Given the limited supply of the patient's blood, any decrease in priming volume in the oxygenator or other components of the extracorporeal circuit greatly enhances the chances for a positive surgery and rapid recovery.

In spite of ongoing advances in extracorporeal circuit technology, there exists an ever-present need for a reduced prime CPB system.

SUMMARY OF THE INVENTION

The present invention provides an improved low prime extracorporeal system including a low prime oxygenator and a low prime combined heat exchanger/reservoir. The dimensions of the oxygenator are optimized so that, in conjunction with a particularly preferred hollow fiber architecture, a prime reduction from currently available models as well as top performance results. Two sizes of oxygenator are disclosed which have the capacity to fulfill the needs of all ranges of patient weights, from the smallest neonatal baby to large adults. The oxygenators share certain preferred dimensions and elements, and essentially just differ in height. The combined heat exchanger/reservoir makes use of a single-pass guided heat exchanger configuration that decouples the heat exchange efficiency from the reservoir blood level.

In one embodiment, the low prime oxygenator, comprises a rigid housing defining an annular oxygenation chamber having a first axial end and a second axial end. A plurality of elongated, hollow, semi-permeable fibers are arranged in an annular bundle in the oxygenation chamber and secured at both axial ends with a potting compound. The bundle substantially fills the oxygenation chamber with the fibers arranged to provide blood flow spaces therebetween, and the opposed ends of the fibers are open to a gas header space formed in the housing outside of the oxygenation chamber. A central blood inlet port is provided in communication with a blood distribution space adjacent one axial end of the oxygenation chamber. A plurality of blood inlets in the housing are formed around the annular oxygenation chamber in communication with the blood distribution space, while a plurality of blood outlets in the housing are formed around the annular oxygenation chamber on the axial end opposite the blood inlets. In an embodiment of the oxygenator suitable for adults, the oxygenator has a prime volume of between 130 and 180 ml and a ratio of oxygen transfer rate to prime volume of at least about 0.34 lpm/min, at a flow rate of about 7 lpm. In an embodiment of the oxygenator suitable for neonatal/infants, the oxygenator has a prime volume of between about 56 ml and 80 ml and an oxygen transfer rate of about 62.5 ml/min/lpm at a flow rate of about 2 lpm.

The blood oxygenator of the present invention desirably has a simplified construction with a rigid housing consisting essentially of five parts, including: an inner core having a radial bottom wall and a cylindrical wall, an outer cylindrical wall concentric about the inner core cylindrical wall defining an annular oxygenation chamber therebetween having a first axial end and a second axial end, a pair of end caps connected to opposite ends of the outer cylindrical wall, and a blood inlet cap secured to the inner core. The inlet cap has a central blood inlet port in communication with a blood distribution space adjacent one axial end of the oxygenation chamber and formed between the inlet cap and the inner core bottom wall. A plurality of blood inlets in the inner core are formed around the blood distribution space in communication with the annular oxygenation chamber. The oxygenator includes a plurality of elongated, hollow, semi-permeable fibers arranged in an annular bundle in the oxygenation chamber and secured at both axial ends with a potting compound. The opposed ends of the fibers are open to a gas header space formed within the end caps outside of the oxygenation chamber. The bundle substantially fills the oxygenation chamber with the fibers having blood flow spaces therebetween. A plurality of blood outlets in the outer cylindrical wall are formed around the annular oxygenation chamber on the axial end opposite the blood inlets causing generally axial flow of blood through the oxygenation chamber and between the hollow fibers. The five parts of the oxygenator are either snap-fit together with O-ring seals, or are bonded with adhesive or UV welds.

The present invention also embodies an extracorporeal system, comprising a combined heat exchanger/blood reservoir and a hollow fiber oxygenator. The reservoir has heat exchange elements located in a separate heat exchange chamber and a blood outlet. The oxygenator includes a blood inlet connected to the blood outlet of the heat exchanger/blood reservoir, and a rigid housing defining an annular oxygenation chamber having a cross-sectional area normal to its axis of between about 24 and 28 square centimeters. The oxygenation chamber has a first axial end and a second axial end, and the housing includes a central blood inlet port in communication with a blood distribution space adjacent one axial end of the oxygenation chamber. A plurality of blood inlets in the housing are formed around the annular oxygenation chamber in communication with the blood distribution space, while a plurality of blood outlets in the housing are formed around the annular oxygenation chamber on the axial end opposite the blood inlets. Finally, a plurality of elongated, hollow, semi-permeable fibers arranged in an annular bundle in the oxygenation chamber and secured at both axial ends with a potting compound. The opposed ends of the fibers are open to a gas header space formed in the housing outside of the oxygenation chamber. The fibers having an aggregate volume that is between 0.5 and 0.6 of the volume in the oxygenation chamber between the potting compound at both axial ends.

A combined heat exchanger/blood reservoir, including a housing topped by a lid together defining a reservoir chamber within, a venous blood inlet in the lid, a heat exchanger within the chamber including a plurality of heat exchange elements, and a blood outlet in a lower portion of the reservoir chamber. The heat exchange chamber is defined by guides closely surrounding the heat exchange elements and extending downward from a location at an upper portion of the reservoir chamber. The heat exchange chamber has an upper inlet open to the venous blood inlet and a lower outlet open to the reservoir chamber so that blood from the venous blood inlet must flow through the heat exchange chamber before reaching the reservoir chamber. Preferably, the guides are concentric tubes defining an annular heat exchange chamber terminating at an elevation about ¼ of the distance from the bottom of the reservoir chamber.

Further objects and advantages of the present invention shall become apparent to those skilled in the art upon reading and understanding the following detailed description of a presently preferred embodiment of the invention.

BRIEF DESCRIPTION OF THE DRAWINGS

FIG. 3a is a sectional exploded view of the oxygenator of FIG. 3;

DESCRIPTION OF THE PREFERRED EMBODIMENTS

Figure 1:
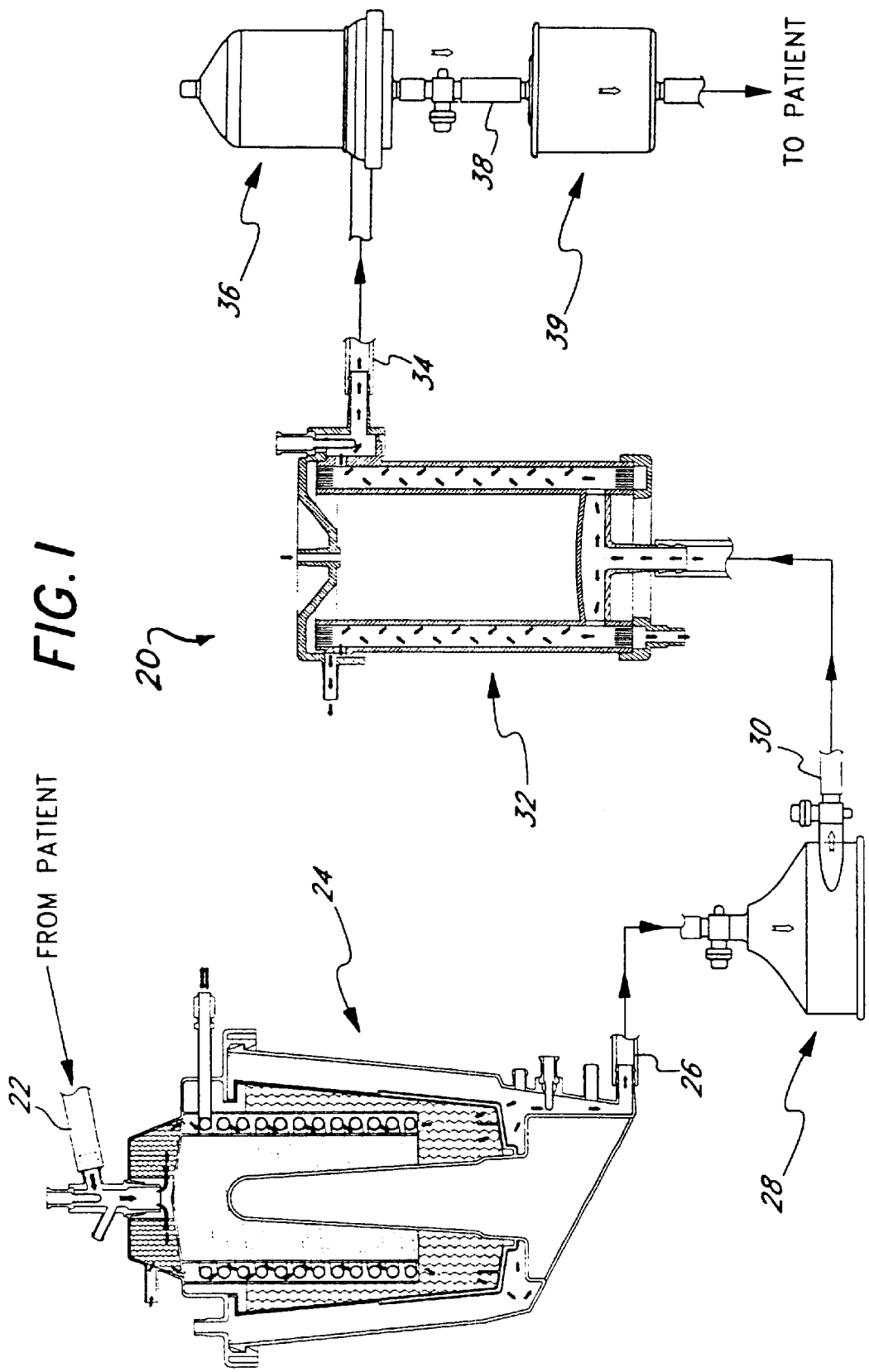
FIG. 1 is a schematic diagram of an extracorporeal circuit including elements of the present invention.

FIG. 1 shows an example of a perfusion system 20 utilizing elements of the present invention including a venous line 22 leading from a patient into a venous input of a heat exchanger/reservoir 24. The reservoir 24 may also include cardiotomy inputs, and the combined cardiotomy and venous fluid is filtered and heat treated before exiting through a lower outlet to a second conduit 26. The conduit 26 leads to an input of a blood pump 28, such as a centrifugal pump as shown, typically controlled by a controller (not shown). The outlet of the pump leads to a third conduit 30 that is connected to an input of a low prime oxygenator 32. Blood is perfusion with oxygen within the oxygenator 32 and passed therefrom through a fourth conduit 34 to an arterial filter 36. The oxygenated blood continues through the arterial filter 36 to an arterial return line 38 that terminates in an arterial cannula (not shown) in the patient. Other components, such as a bubble detector 39, may be provided in the return line 38, as is well known in the art.

Adult Heat Exchanger/Reservoir

Figure 2:
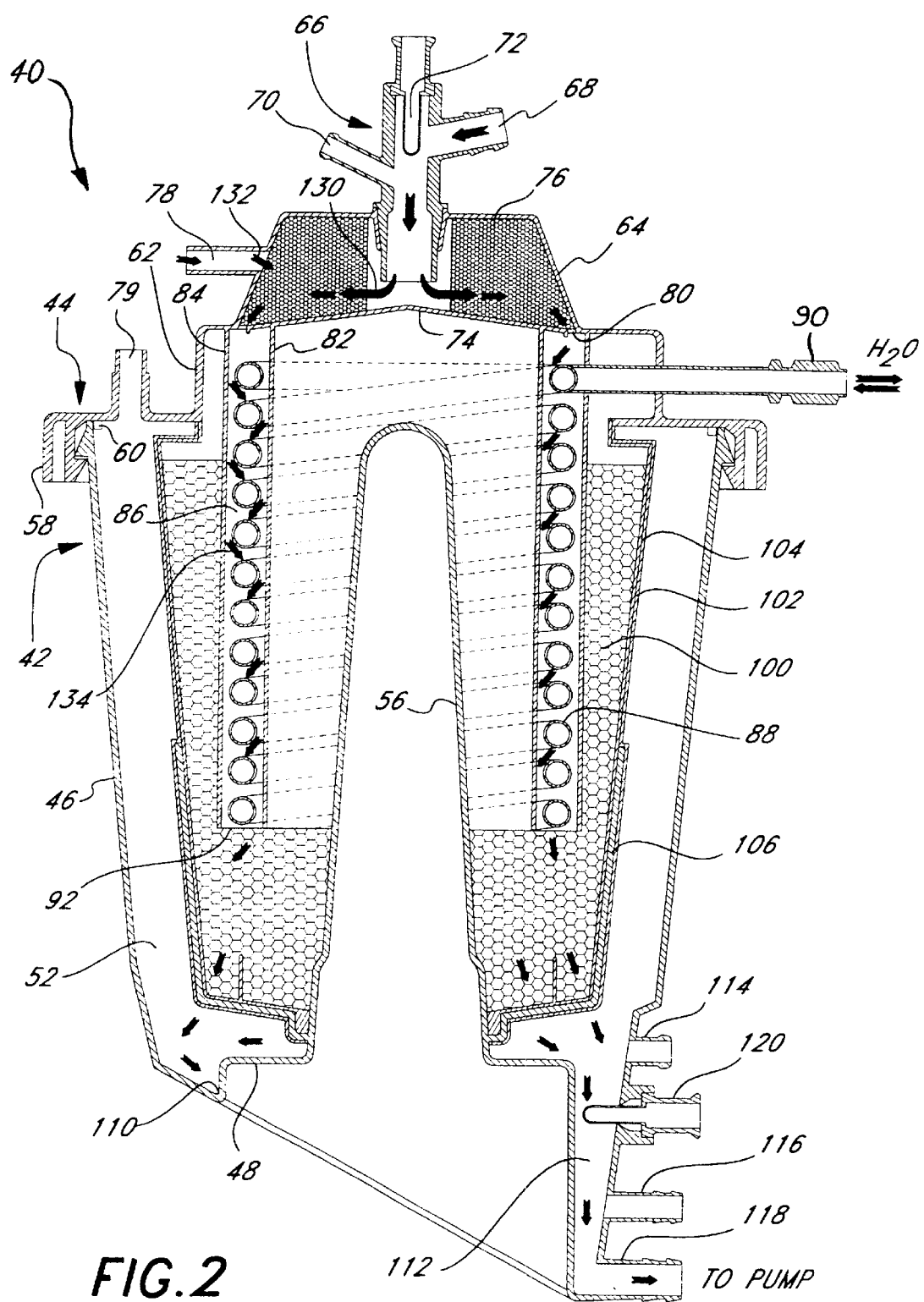
FIG. 2 is a cross-sectional view of a heat exchanger/reservoir for use in adult extracorporeal circuits.

FIG. 2 is a cross sectional view through an exemplary heat exchanger/reservoir 40 sized for use in an adult extracorporeal circuit. The heat exchanger/reservoir 40 comprises a lower housing 42 topped by a lid 44. The housing 42 comprises a slightly upwardly and outwardly tapered cylindrical outer wall 46 and a reservoir floor 48 that, together with the lid 44, define within a reservoir chamber 52. The heat exchanger/reservoir 40 may be adapted in conventional ways to be secured in a location adjacent to an operating table.

An elongated, conical, central spacer 56 extends upward from the reservoir floor 48 into proximity with the lid 44. The central spacer 56 is preferably concentrically positioned within the outer wall 46 to define an inner boundary of the reservoir chamber 52. The reservoir chamber 52 thus comprises a tall, generally annular space defined within the housing 42.

The lid 44 includes an outer flange 58 surrounding the top rim of the outer wall 46. An O-ring 60 provides a seal between the housing 42 and the lid 44. Inward from the flange 58, the lid 44 includes an upwardly projecting first turret 62, and a second smaller turret 64 formed above the first turret. The second turret 64 has a central opening in a top wall for receiving a venous inlet fitting 66. The fitting 66 extends upward and branches outward into a venous inlet port 68, and an upper sampling port 70. A third aperture may be provided in the fitting 66 to receive an inlet blood temperature probe 72. The venous inlet fitting 66 extends downward into a space created within the second turret 64 and bounded on the bottom side by a conical flow guide 74. An annular debubbler filter 76 is provided within the space in the second turret 64. One or more cardiotomy inlets 78 may also be provided in the side wall of the second turret 64.

The reservoir 40 may be adapted for conventional venous gravity drainage wherein a gas vent 79 in the lid 44 remains open. In this mode, the chamber 52 is not sealed from the outside atmosphere. More recently, advances in minimally invasive surgical techniques have dictated the use of smaller and smaller venous cannulae, and a negative pressure in the venous return line may be advantageous. In this mode, a source of vacuum may be connected with the chamber 52 to help pull venous blood from the patient, such as by attaching a vacuum line (not shown) to the gas vent 79. This seals the chamber 52 from the outside atmosphere and creates a negative pressure within.

A plurality of heat exchange chamber inlets 80 are provided between the outer edges of the flow guide 74 and an internal corner formed between the first and second turrets 62, 64. The inlets 80 may be a regular series of apertures, or slots, or may be formed by an annular space surrounding the flow guide 74 interrupted by spokes connecting the flow guide with the lid 44.

A generally cylindrical inner heat exchange chamber wall or guide 82 extends downward from the flow guide 74 into the reservoir chamber 52. The inner heat exchange guide 82 is concentrically spaced around the central spacer 56. A generally cylindrical outer heat exchange guide 84 depends downward from the first turret 62 to concentrically surround the inner heat exchange guide 82, and defines an annular heat exchange chamber 86 therebetween. A plurality of heat exchange elements or coils 88 internally defining one or more fluid flow paths are helically disposed in the annular heat exchange chamber 86. Preferably, a single heat exchange inlet conduit 90, in cooperation with an outlet heat exchange conduit (not shown), supplies a flow of heat transfer medium to the interior of the coils 88. In the preferred embodiment, the heat transfer medium is water, although other mediums are contemplated.

The annular heat exchange chamber 86 defined between the guides 82, 84 extends downward from the lid 44 a substantial distance toward the reservoir floor 48. In a preferred embodiment, the guides 82, 84 terminate at a heat exchange outlet 92 that is located above the reservoir floor 48 a distance of approximately ¼ of the total height of the reservoir chamber 52. This relative distance may be modified depending on the total volume of the reservoir chamber 52, and its radial dimensions.

A large defoamer element 100 closely surrounds the outer heat change guide 84. The defoamer element 100 continues radially inward underneath the annular heat exchange chamber 86 into contact with the central spacer 56. The defoamer element 100 may be a variety of constructions, but is preferably a polymer mesh treated with a defoaming substance. A support sleeve 102 surrounds and contains the defoamer element 100. The support sleeve 102 desirably rigidly attaches at the top to the lid 44, and at the bottom to the central spacer 56, or to the reservoir floor 48. The support sleeve 102 may take a variety of forms, but is preferably a plastic member having a grid-like or otherwise perforated configuration. An outer polyester filter or sock 104 surrounds the supports sleeve 102 and contains a non-woven filter 106 around the lower end thereof. The non-woven filter 106 has a cup shape and extends upward above the heat exchange outlet 92.

The reservoir floor 48 defines a peripheral flow channel 110 which gradually transitions into a deep drain well 112 on one circumferential side. A number of apertures are formed in the housing adjacent the drain well 112. Namely, a lower sampling port 114, a hemo concentration line 116, and a blood outlet port 118, all communicate through the apertures with the drain well 112. A fourth aperture may receive a lower blood temperature probe 120.

Operation of Adult Heat Exchanger/Reservoir

In operation, venous blood enters the heat exchanger/reservoir 40 through the venous inlet port 68. The venous blood travels downward through the fitting 66 and radially outward through the debubbler filter 76 as indicated by the flow arrows 130. Fluid aspirated through the cardiotomy lines enters through the cardiotomy inlets 78 and passes through the debubbler filter 76 as indicated by the flow arrows 132. In this manner, venous inlet blood does not mix with cardiotomy fluid before passing through the debubbler filter 76.

The cardiotomy fluid and venous blood pass downward through the heat exchange chamber inlets 80 into the annular heat exchange chamber 86. The blood then flows by gravity (or under the influence of a slight vacuum, if vacuum-assisted venous drainage is desired) across the heat exchange coils 88 in a single pass, as indicated by flow arrows 134. The heat treated blood exits the heat exchange chamber 86 into the reservoir chamber 52 through the heat exchange outlet 92. After passing through the heat exchange chamber 86, blood continues downward and outward through the defoamer element 100, support sleeve 102, non-woven filter 106, and polyester filter 104, into the space between the polyester filter and the outer wall 46. The blood level under the heat exchange chamber 86 and within the sock 104 may reach or exceed that of the heat exchange outlet 92, but desirably does not crest over the top edge of the non-woven filter 106 to ensure proper filtration. The blood then continues through the flow channel 110 into the drain well 112, and out through the outlet port 118.

One advantage of the present heat exchanger/reservoir 40 is the provision of a separate heat exchange chamber 86 within the reservoir. With such an arrangement, the ratio of the surface area of the heat exchange coils 88 to the volume of blood in the heat exchange chamber 86 is maximized, and the blood is guided across every coil. The performance of the heat exchanger is thus not dependent on the level of blood within the reservoir. As will be appreciated by those of skill the art, separate heat exchange chambers within the reservoir other than the annular columnar embodiment shown may be equally effective as long as the result is to decouple the heat exchange efficiency from the reservoir blood level. In addition, heat transfer elements other than the coils shown may be used, such as fins or straight tubes.

Adult Low Prime Oxygenator

Figure 3:
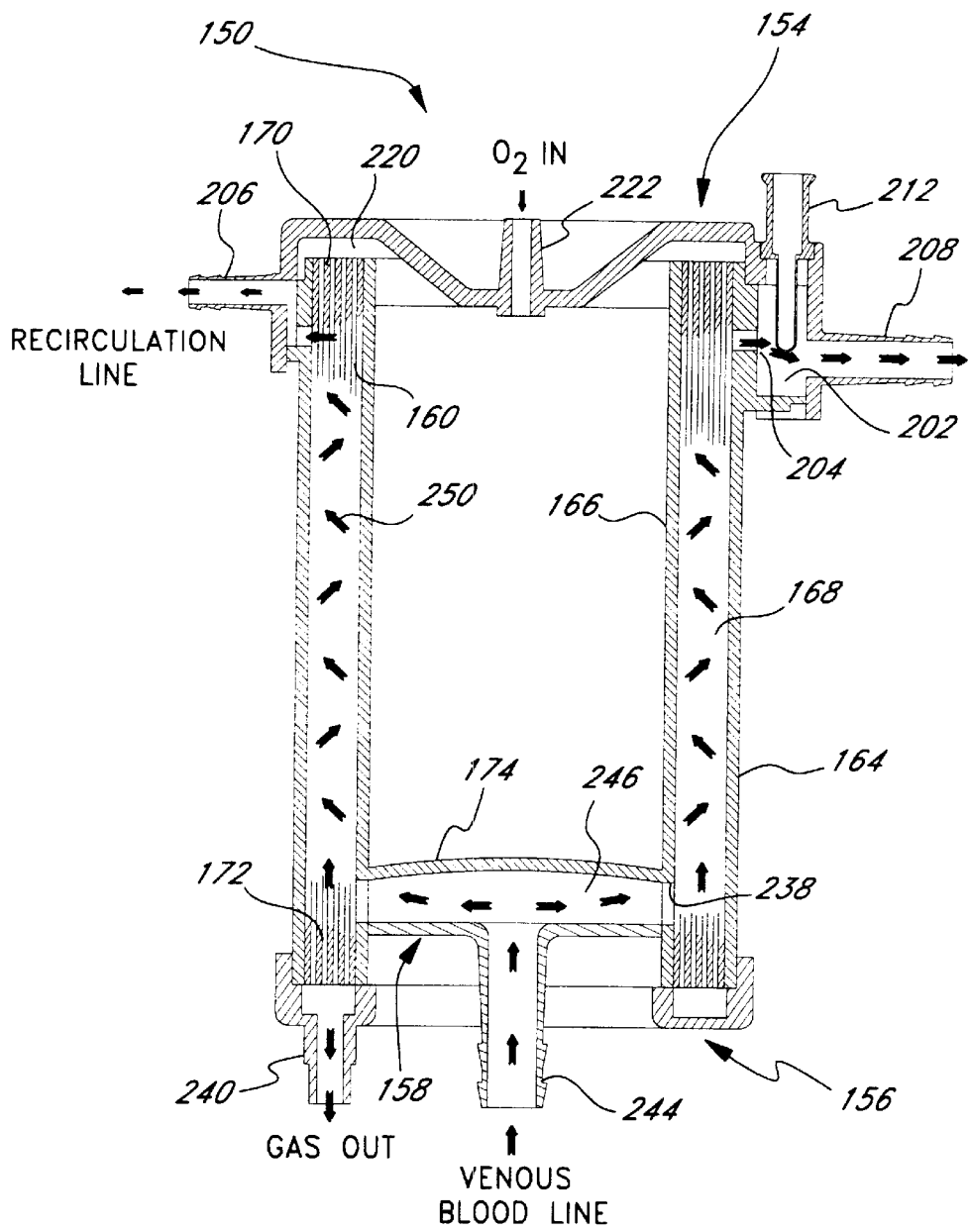
FIG. 3 is a cross-sectional view of a low prime volume oxygenator for use in adult extracorporeal circuits.

As seen FIG. 1, a blood pump 28 impels blood from port 118 to a blood oxygenator 32. Although the previously described heat exchanger/reservoir 40 may be coupled with a variety of oxygenators, a particularly preferred oxygenator 150 is seen in FIGS. 3 and 3a. The oxygenator 150 is a low prime membrane oxygenator having a single blood inlet and outlet, and single gas inlet and outlet.

As seen exploded in FIG. 3a, the main components of the oxygenator 150 comprise a central, cylindrical housing 152, a top cap 154 on one axial end of the housing, and a bottom cap 156 and a blood inlet cap 158 on an opposite axial end of the housing. The housing 152 is preferably cylindrical, but may be other shapes, and is concentrically disposed about an axis (not shown). The components of the housing 152, top cap 154, bottom cap 156, and blood inlet cap 158, are preferably molded of plastic, biocompatible materials. Biocompatible coatings, such as Duraflo® available from Baxter Healthcare Corporation, may be provided on the plastic components of the oxygenator 150 to reduce blood interactions.

One primary advantage of the oxygenator 150 is the small number of parts. In addition to those mentioned above, the only other components of the oxygenator 150 are a plurality of hollow, semi-permeable fibers 160 (partially shown in the chamber 168) extending generally axially within housing 152, and potting regions 170, 172 at both ends of the fibers and housing. The respective components, except the hollow fibers 160, are easily molded and attached together using a variety of means. For instance, the mating parts may be provided with interfering ribs or latches in conjunction with a sealing mechanism, such as O-rings, to enable a snap-fit assembly. Alternatively, the parts may be more permanently bonded together, such as with a biocompatible adhesive, or, more preferably, with ultraviolet (UV) welding.

The specific structural attributes of the low prime oxygenator 150 will now be described in more detail. The central housing 152 comprises an outer wall 164 concentrically disposed about an inner wall 166. An elongated annular oxygenation chamber 168 is defined between the inner surface of the outer wall 164 and the outer surface of the inner wall 166. The hollow fibers 160 extend generally axially within the oxygenation chamber 168 and are rigidly secured within the chamber between an upper potting region 170, and a lower potting region 172. The potting regions 170 and 172 delimit the oxygenation chamber 168 at each axial end. As is well-known in the art, the hollow fibers 160 are positioned and secured with potting material at both ends, which material is then severed perpendicular to the axis to expose open ends of each individual fiber. The potted bundle of fibers 160 is then sealed in place flush with both ends of the housing 152. The housing 152 further includes a bottom wall 174 extending across, and preferably molded integrally with, the inner wall 166 at a distance from the lower extremity of the housing.

The top cap 154 comprises a top wall 180 having a peripheral side wall 182 joined thereto. As seen in FIG. 3, the top cap 154 fits over the top end of the housing 152 so that mating portions of the side wall 182 and outer wall 164 are in registry. More specifically, an inner shoulder 184 in the top cap 154 contacts a step 186 at the top end of the outer wall 164. In addition, a portion of the side wall 182 extends around a small flange 188, and a skirt 190 extends downward around and in contact with a large flange 192.

With reference to FIG. 3, a blood outlet manifold is defined within the top cap 154 and outside of the housing 152. More specifically, the side wall 182 defines a small annular space 200 adjacent the small flange 188. The small flange 188 and annular space 200 extend substantially around the periphery of the housing 152. The skirt 190 comprises an outwardly bulged portion on one side of the side wall 182 and defines a larger space 202. The smaller space 200 and larger space 202 are in fluid communication to define the blood outlet manifold surrounding a plurality of oxygenation chamber outlets 204. A recirculation port 206 extends radially outward from the side wall 182 at a location that is diametrically opposed to the large space 202 and a blood outlet port 208 extending radially outward from the skirt 190. An aperture 210 may be provided in the top cap 154 to receive a temperature probe 212 for measuring the temperature of blood within the large space 202.

The top wall 180 of the top cap 154 is shaped to define an annular gas header space 220 adjacent the upper potting region 170 and sealed from the blood outlet manifold. A gas inlet port 222 in the center of the top cap 154 opens into a large central gas manifold bordered by the inner wall 166, bottom wall 174, and top cap 154. The open ends of the hollow fibers 160 adjacent the gas header space 220 are in fluid communication with this gas chamber.

Still with reference to FIG. 3a, the bottom cap 156 comprises a bottom wall 230, an inner skirt 232, and an outer skirt 234. The inner wall 166 of the housing 152 includes a lower cylindrical portion 236 below the bottom wall 174. A number of circumferential slots or apertures define oxygenation chamber inlets 238 between this lower portion 236 and the bottom wall 174. Although not shown, the lower portion 236 is desirably integrally molded with the inner wall 166 and bottom wall 174 to define an inner core of the housing 152. The bottom cap 156 fits over the lower end of the housing 152 with the inner skirt 232 in sealed contact with the lower portion 236, and the outer skirt 234 surrounding and in sealed contact with the outer wall 164. The bottom wall 230 of the bottom cap 156 is spaced from the lower potting region 172 to define an annular lower manifold 239 (FIG. 3) in fluid communication with the open ends of the hollow fibers 160 secured within the lower potting region 172. A gas outlet port 240 also in fluid communication with the manifold 239 extends downward from the bottom wall 230 on one side thereof.

The blood inlet cap 158 comprises a radially disposed circular flange 242 and an axial blood inlet port 244. The flange 242 fits snugly within the inner surface of the lower portion 236 of the inner wall 166 and is secured thereto. The flange 242 is thus spaced from the bottom wall 174 to define a blood distribution space 246 therebetween, with the chamber inlets 238 desirably evenly arranged around the distribution space circumference.

The adult oxygenator 150 preferably has a prime volume of between 130–180 ml.

Operation of the Adult Low Prime Oxygenator

With reference to FIG. 3, the respective blood and gas flows through the oxygenator 150 are shown. Blood enters through the central lower inlet port 244 and is evenly distributed radially outward in all directions in the space 246. The blood passes outward through the chamber inlets 238 into the oxygenation chamber 168. As seen by the nonlinear blood flow arrows 250, blood passes upward through the chamber 168 in the spaces formed between the hollow fibers 160.

In a preferred embodiment, the hollow fibers 160 are arranged in sequential layers of fiber mats, with the fibers in adjacent mats being helically angled with respect to each other. In a first example, the angle of fibers in each mat is in the same helical sense, while in a second example, the angle of fibers in adjacent mats are in the opposite helical sense. In the former example, the blood passes between the fibers in a generally helical path through the oxygenation chamber 168, while in the latter example, the blood passes between the fibers in a zigzag fashion from one end of the chamber 168 to the other. Various configurations of hollow fiber architectures are available for use with the low prime oxygenator, such as for example in PCT publication No. WO 97/08933, which is hereby expressly incorporated by reference. Exemplary hollow fiber architectures are shown and described in more detail with respect to FIGS. 6a and 6b.

Blood flows through the chamber 168 as shown by the arrows 250 from the inlets 238 to the outlets 204. As mentioned above, the inlets 238 and outlets 204 are provided around substantially the entire circumference of the housing 152 to help ensure even distribution of the blood flow within the chamber 168. Because of the circular disposition of the inlets 238 and outlets 204, the blood flows substantially axially within the chamber 168 past the hollow fibers 160. The now oxygenated blood fills the annular region defined by the spaces 200 and 202 and is available for outlet through the recirculation port 206 and/or blood outlet port 208.

Gas flows into the oxygenator 150 through inlet port 222 and into the region in communication with the gas header space 220. As mentioned, the hollow fibers 160 are open at the top end of the upper potting region 170 and the gas flows into the hollow fibers and continues through the fiber lumens to the lower manifold 239. The inlet gas is preferably pure or nearly pure oxygen which permeates outward through the semi-permeable tubular wall of each individual hollow fiber 160 into the blood which is passing in a counter direction, thus raising the oxygen partial pressure of the blood. The impetus for the migration of gas molecules through the tubular fiber walls is a differential partial pressure of each respective gas. Carbon dioxide permeates inwardly from the blood into each individual fiber lumen, thus lowering the carbon dioxide partial pressure of the blood. The end result is that the blood absorbs oxygen and gives off carbon dioxide into the gas stream. The gas exits the open ends of hollow fibers 160 into the lower manifold 239 and is exhausted through the gas outlet port 240.

Neonatal/Infant Heat Exchanger/Reservoir

Figure 4:
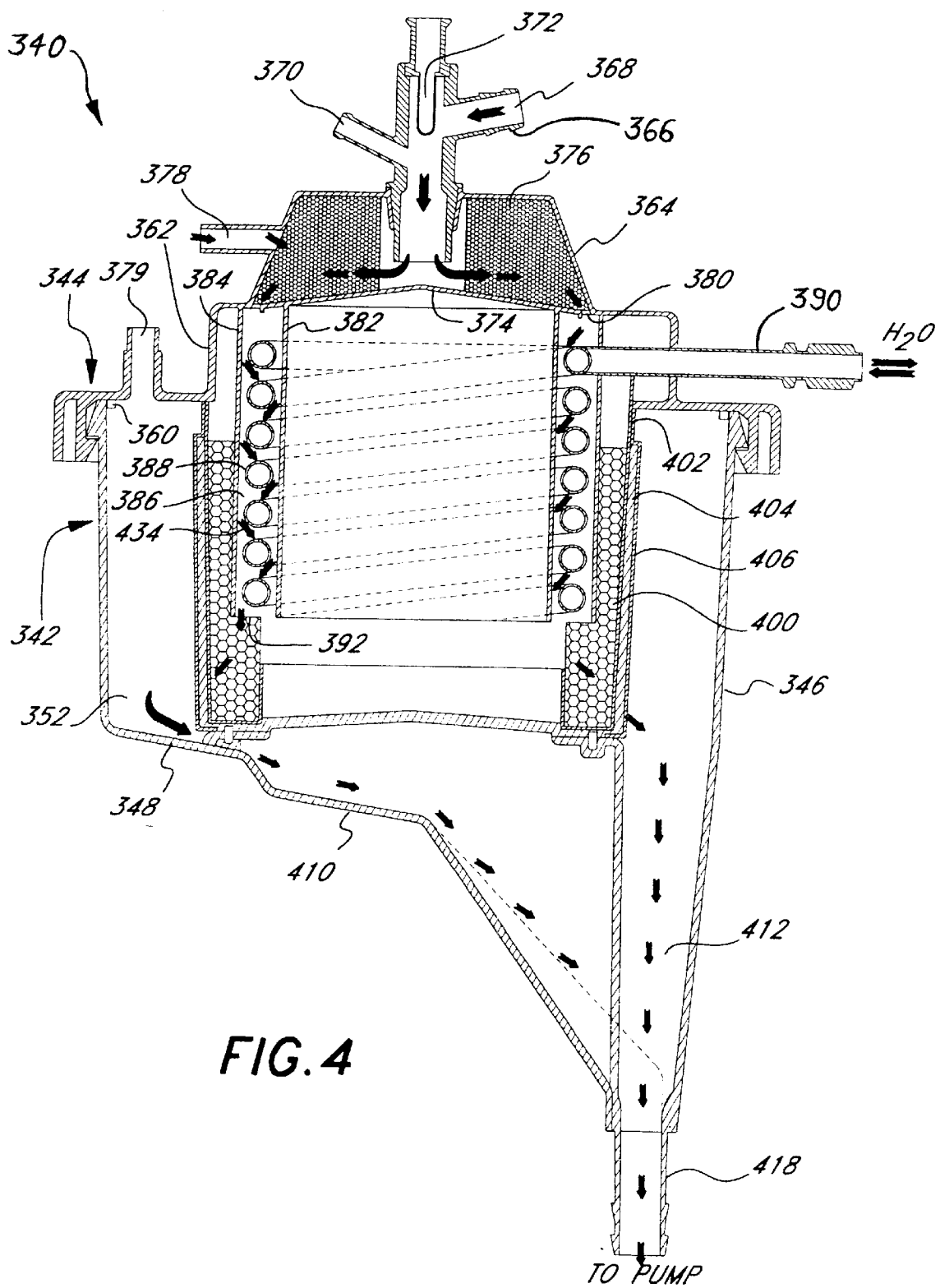
FIG. 4 is a cross-sectional view of a heat exchanger/reservoir for use in neonatal/infant extracorporeal circuits.

FIG. 4 is a cross sectional view through an exemplary heat exchanger/reservoir 340 sized for use in an neonatal/infant extracorporeal circuit. The reservoir 340 is similar in many respects to the adult reservoir 40 described above, and as such, like elements are numbered in parallel in the 300 and 400 range and may not be described in as great detail.

The heat exchanger/reservoir 340 comprises a lower housing 342 topped by a lid 344. The housing 342 comprises a slightly upwardly and outwardly tapered cylindrical outer wall 346 and a reservoir floor 348 that, together with the lid 344, define within a reservoir chamber 352. An O-ring 360 provides a seal between the housing 342 and lid 344. Conventional mounting means may be provided to secure the heat exchanger/reservoir 340 in a location adjacent to an operating table. In contrast to the adult reservoir 40 described above, the neonatal/infant reservoir 340 does not include a central conical spacer, and the reservoir chamber 352 thus comprises a generally cylindrical volume defined within the housing 342.

As before, the lid 344 includes an upwardly projecting first turret 362, and a second smaller turret 364 formed above the first turret. The second turret 364 has a central opening in a top wall for receiving a venous inlet fitting 366 that extends upward and branches outward into a venous inlet port 368, and an upper sampling port 370. A third aperture may be provided in the fitting 366 to receive an inlet blood temperature probe 372. The venous inlet fitting 366 extends downward into a space created within the second turret 364 and bounded on the bottom side by a conical flow guide 374. An annular debubbler filter 376 is provided within the space in the second turret 364. One or more cardiotomy inlets 378 may also be provided in the side wall of the second turret.

The reservoir 340 may be adapted for conventional venous gravity drainage in which a gas vent 379 in the lid 344 is open so that the chamber 352 is not sealed from the outside atmosphere. Alternatively, a vacuum line (not shown) may be attached to the gas vent 379 which seals the chamber 352 from the outside atmosphere and creates a negative pressure within to help pull venous blood from the patient.

A plurality of heat exchange inlets 380 are provided between the outer edges of the flow guide 374 and an internal corner formed between the first and second turrets 362, 364. As in the earlier embodiment, the inlets 380 may be a regular series of apertures, or slots, or may be formed by an annular space surrounding the flow guide 374 interrupted by spokes connecting the flow guide with the lid 344.

A generally cylindrical inner heat exchange chamber wall or guide 382 extends downward from the flow guide 374 into the reservoir chamber 352. The inner heat exchange guide 382 is concentrically spaced within the outer wall 346. A generally cylindrical outer heat exchange guide 384 depends downward from the first turret 362 to surround the inner heat exchange guide 382 and define an annular heat exchange chamber 386 therebetween. A plurality of heat exchange elements or coils 388 internally defining one or more fluid flow paths are helically disposed in the annular heat exchange chamber 386. Preferably, a single heat exchange inlet conduit 390, in cooperation with an outlet heat exchange conduit (not shown), supplies a flow of heat transfer medium to the interior of the coils 388.

The annular heat exchange chamber 386 defined between the guides 382, 384 extends downward from the lid 344 a substantial distance toward the reservoir floor 348. In a preferred embodiment, the guides 382, 384 terminate at a heat exchange outlet 392 that is located above the reservoir floor 348 a distance of approximately ¼ of the total height of the reservoir chamber 352. Again, this relative distance may be modified depending on the total volume of the reservoir chamber 352, and its radial dimensions, and may be different from the configuration of the adult reservoir 40.

The neonatal/infant reservoir 340 includes a series of concentric filters surrounding the heat exchange chamber 386 as described previously. Thus, the reservoir 340 preferably includes a large defoamer filter 400 surrounded by a support sleeve 402, with an outer polyester sock 404 and a non-woven filter 406 around the lower end thereof. The non-woven filter 406 extends above the height of the heat exchange outlet 392 proportionally higher in the neonatal/infant reservoir 340 than in the adult reservoir 40.

The reservoir floor 348 defines a flow channel 410 that provides a gradual transition from the floor to a deep drain well 412. A number of apertures may be formed in the housing adjacent the drain well 412, although only a blood outlet port 418 is shown.

Operation of the Neonatal/Infant Heat Exchanger/Reservoir

The operation of the neonatal/infant reservoir 340 is as described above with respect to the adult reservoir 40, with venous blood entering through the venous inlet port 368 and exiting from the lower outlet 418. As before, venous inlet blood does not mix with cardiotomy fluid before passing through the debubbler filter 376.

Within the chamber 352, cardiotomy fluid and venous blood pass downward through the heat exchange inlets 380 into the annular heat exchange chamber 386. The blood then flows by gravity over the exchange coils 388 in a single pass, as indicated by flow arrows 434, and exits into the reservoir chamber 352 through the heat exchange outlet 392. After passing through the heat exchanger, blood continues downward and outward through the defoamer element 400, support sleeve 402, non-woven filter 406, and polyester filter 404, into the space between the polyester filter and the outer wall 346. The increased height of the top edge of the non-woven filter 406 is needed to prevent cresting and ensure proper filtration of the blood because of the smaller volume, and thus more variable blood level in the reservoir chamber 352. After being filtered, the blood then continues through the flow channel 410 and into the drain well 412.

Neonatal/Infant Low Prime Oxygenator

Figure 5:
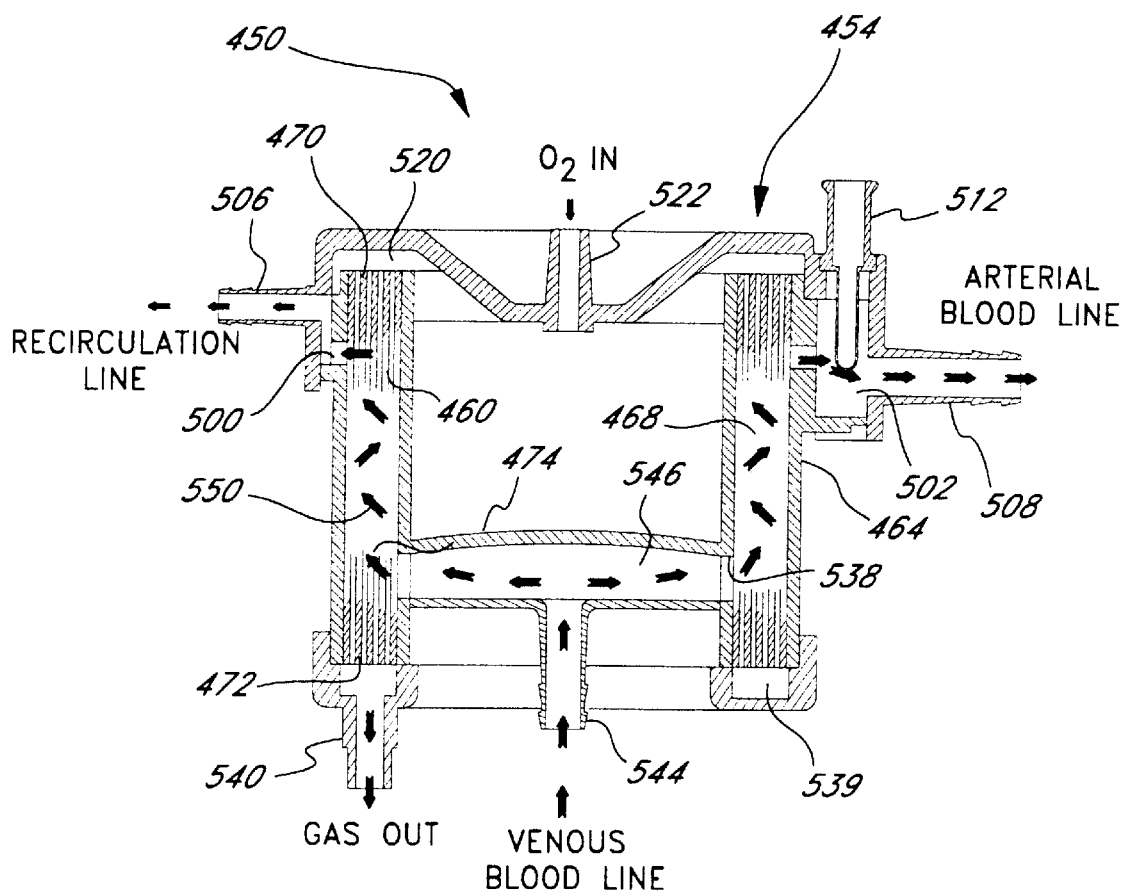
FIG. 5 is a cross-sectional view of a low prime volume oxygenator for use in neonatal/infant extracorporeal circuits.
Figure 5A:
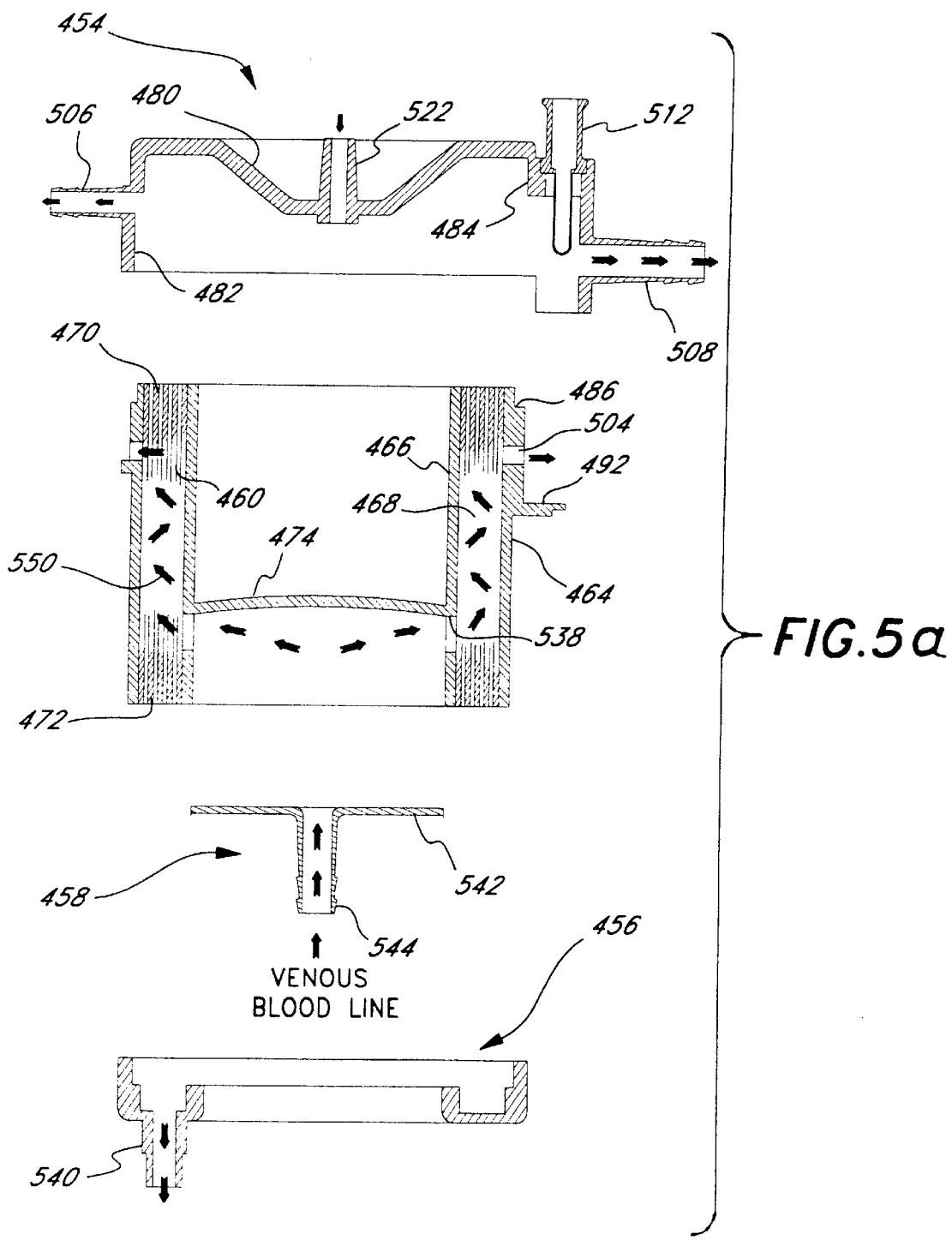
FIG. 5a is a sectional exploded view of the oxygenator of FIG. 5.

As seen in FIG. 1, a blood pump 28 impels the blood from reservoir outlet port 418 to a blood oxygenator 32. Although the previously described heat exchanger/reservoir 340 may be coupled with a variety of oxygenators, a particularly preferred oxygenator 450 suitable for use with neonatals or infants is seen in FIGS. 5 and 5a. The oxygenator 450 is similar in many respects to the adult oxygenator 150 described above, and as such, like elements are numbered in parallel in the 400 and 500 range and may not be described in as great detail.

As seen exploded in FIG. 5a, the main components of the oxygenator 450 comprise a central, cylindrical housing 452, a top cap 454 on one axial end of the housing, and a bottom cap 456 and a blood inlet cap 458 on an opposite axial end of the housing. The housing 452 is preferably cylindrical, but may be other shapes, and is concentrically disposed about an axis (not shown). The components of the housing 452, top cap 454, bottom cap 456, and blood inlet cap 458, are preferably molded of plastic, biocompatible materials. Biocompatible coatings, such as Duraflo® available from Baxter Healthcare Corporation, may be provided on the plastic components of the oxygenator 450 to reduce blood interactions.

As in the earlier embodiment, the oxygenator 450 has a very small number of parts for ease of manufacture and assembly. In addition to those mentioned above, the only other components of the oxygenator 450 are a plurality of hollow, semi-permeable fibers 460 extending generally axially within housing 452, and potting regions at both ends of the fibers and housing. The respective components, except the hollow fibers 460, are easily molded and attached together using a variety of means. For instance, as described above, a snap-fit assembly, biocompatible adhesive, or, more preferably, ultraviolet (UV) welding may be utilized.

The central housing 452 comprises an outer wall 464 concentrically disposed about an inner wall 466. An elongated annular oxygenation chamber 468 is defined between the inner surface of the outer wall 464 and the outer surface of the inner wall 466. The hollow fibers 460 extend generally axially within the oxygenation chamber 468 and are rigidly secured within the chamber between an upper potting region 470, and a lower potting region 472. The housing 452 further includes a bottom wall 474 extending across the inner wall 466 and spaced from the lower extremity of housing.

The top cap 454 comprises a top wall 480 having a peripheral side wall 482 joined thereto. As seen in FIG. 5a, the top cap 454 fits over the top end of the housing 452 so that an inner shoulder 484 in the top cap 454 contacts a step 486 at the top end of the outer wall 464. In addition, a portion of the side wall 482 extends around a small flange 488, and a skirt 490 extends downward around and in contact with a large flange 492.

As in the first embodiment, and with reference to FIG. 5, a blood outlet manifold is defined within the top cap 454 and outside of the housing 452. More specifically, the side wall 482 is shaped to define a small annular space 500 between a plurality of oxygenation chamber outlets 504 and a recirculation port 506. A skirt 490 comprises an outwardly bulged portion on one side of the side wall 482 and defines a larger space 502 between the oxygenation chamber outlets 504 and a blood outlet port 508 extending radially outward from the skirt 490. The smaller space 500 and larger space 502 are in fluid communication to define the blood outlet manifold surrounding the oxygenation chamber outlets 504. An aperture may be provided in the top cap 454 to receive a temperature probe 512 for measuring the temperature of blood within the large space 502.

The top wall 480 of the top cap 454 is shaped to define an annular gas header space 520 adjacent the upper potting region 470 and sealed from the blood outlet manifold. A gas inlet port 522 in the center of the top cap 454 opens into a large central gas manifold bordered by the inner wall 466, bottom wall 474, and top 454. The open ends of hollow fibers 460 adjacent the gas header space 520 are in fluid communication with this gas chamber.

Still with reference to FIG. 5a, a number of circumferential slots or apertures in the inner wall 466 define oxygenation chamber inlets 538. The bottom cap 456 fits over the lower end of the housing 452 with an inner skirt 532 in sealed contact with the lower portion of the inner wall, and an outer skirt 534 surrounding and in sealed contact with the outer wall 464. The bottom cap 456 is spaced from the lower potting region 472 to define an annular lower manifold 539 (FIG. 5) in fluid communication with the open ends of the hollow fibers 460 secured within the lower potting region 472. A gas outlet port 540 in fluid communication with the manifold 539 extends downward from the bottom cap 456 on one side thereof.

The blood inlet cap 458 comprises a radially disposed circular flange 542 and an axial blood inlet port 544. The flange 542 fits snugly within the lower portion of the inner wall 466 and is secured thereto. The flange 542 is thus spaced from the bottom wall 474 defining a blood distribution space 546 therebetween, with the chamber inlets 538 desirably evenly arranged around the distribution space circumference.

The neonatal/infant oxygenator 450 preferably has a prime volume of between 56–80 ml.

Operation of the Neonatal/Infant Low Prime Oxygenator

With reference to FIG. 5, the respective blood and gas flows through the oxygenator 450 are shown. Blood enters through the lower inlet port 544 and is evenly distributed radially outward in all directions in the space 546. The blood passes outward through the chamber inlets 538 into the oxygenation chamber 468. As seen by the nonlinear blood flow arrows 550, blood passes upward through the chamber 468 in the spaces formed between hollow fibers 460.

The blood flows substantially axially through the chamber 468 as shown by the arrows 550 from the inlets 538 to the outlets 504 and is evenly distributed therein by the circular arrangement of the inlets and outlets.

Gas flows into the oxygenator 450 through inlet port 522 and into the region in communication with the gas header space 520. Oxygen permeates outward through the semipermeable tubular wall of each individual hollow fiber 460 into the blood that is passing in a counter direction, while carbon dioxide permeates inwardly from the blood into each individual fiber lumen. The gas exits the open ends of hollow fibers 460 into the lower manifold 539 and is exhausted through the gas outlet port 540.

Hollow Fiber Architecture

Figure 6A:
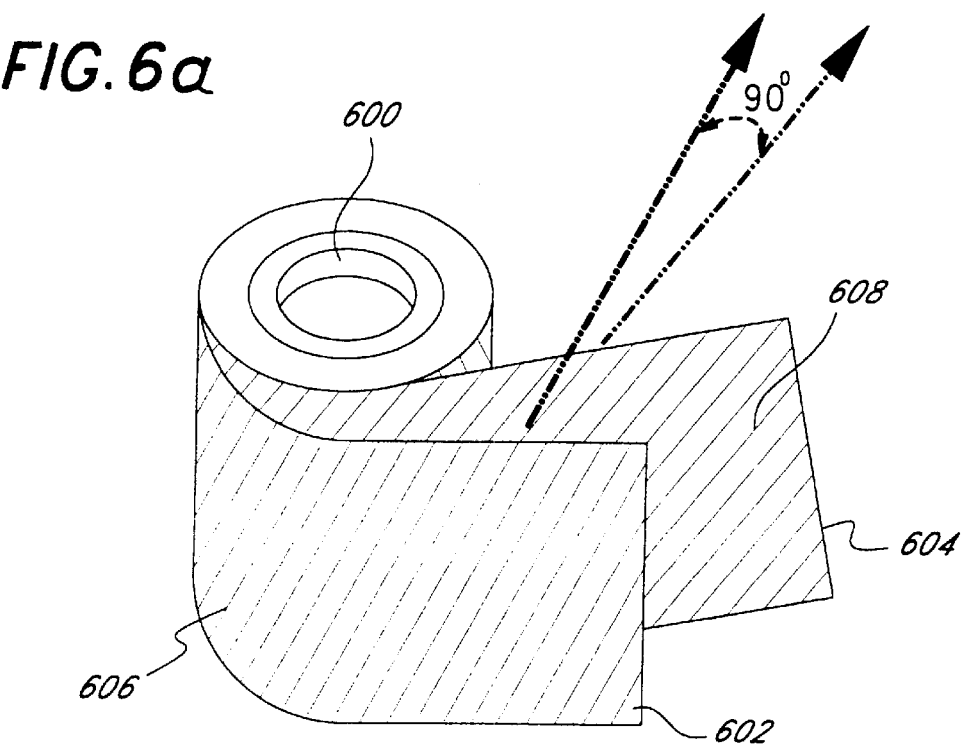
FIG. 6a is a perspective schematic view of a step in the assembly of an exemplary hollow fiber bundle.
Figure 6B:
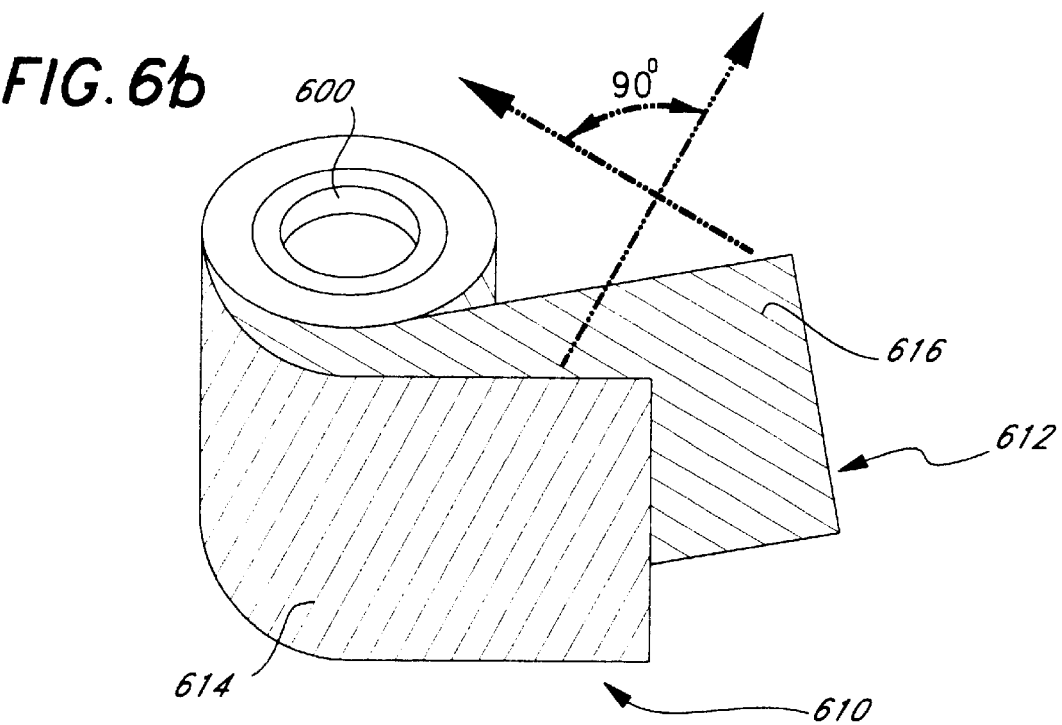
FIG. 6b is a perspective schematic view of a step in the assembly of an another exemplary hollow fiber bundle.

Of course there are a number of different configurations of hollow fibers that may be used with the present oxygenators, but a particular preferred arrangement of layered sheets of fibers produces optimum performance. With reference to FIGS. 6a and 6b, two exemplary embodiments of layered sheets of fibers are shown. Both of these embodiments show layers of fibers being spirally wrapped around a cylindrical core 600, which is removed after an annular fiber bundle is assembled. Alternatively, the layers of hollow fibers may be spiral wound around the inner wall 166 or 466 of one of the two oxygenators, prior to assembling the outer wall thereover. For the sake of manufacturing efficiency, however, a separate core is used to wind the layers of fibers, which are then removed and separately assembled with the other oxygenator parts. Those skilled in the art will recognize that various fabrication methods are possible.

In FIG. 6a, a first layer 602 and a second layer 604 are wound around the core 600. Both the first and second layers 602, 604 comprise a plurality of hollow fibers joined together in a parallel, spaced array with monofilaments, or other similar expedient. A first plurality of fibers 606 in the first layer 602 are arranged at an angle with respect to the axis of the core, while a second plurality of fibers 608 in the second layer 604 are arranged at a different angle. The angles that both the first and second pluralities of fibers 606, 608 make with the axis are in the same rotational sense, and are preferably less than 45°. Furthermore, the angles the two fiber pluralities make are desirably within 15° of each other, more desirably about 9°, as shown. When the complete fiber bundle has been wound and assembled in the oxygenator, the layers are spirally wound, while the individual fibers are helically wound. In the embodiment of FIG. 6a, blood flow through the oxygenation chamber will follow a non-linear path between the alternately angled fibers, and will generally be guided helically around the annular space.

In contrast, the embodiment of FIG. 6b includes a first fiber layer 610 and a second fiber layer 612, wherein a first plurality of fibers 614 and a second plurality of fibers 616 are angled in the opposite rotational sense around the core 600. Again, the angles that both the first and second pluralities of fibers 614, 616 make with the axis are preferably less than 45°, and desirably the included angle therebetween is about 90°. This arrangement induces non-linear and generally axial flow of blood between the alternately angled fibers.

In both fiber embodiments shown in FIGS. 6a and 6b, the two layers of fibers are desirably joined together in a mat prior to spirally winding them about the core. That is, the two joined layers comprise a mat that is then spirally wound in the core. This mat is preferably assembled well before the oxygenator assembly, which facilitates automation and the rapid manufacture of the present oxygenator. One suitable source of such fiber layers is Akzo Nobel N.V. of Arnhem, Netherlands, although other sources are available.

Low Prime Extracorporeal Circuit

The present invention provides improvements over prior extracorporeal circuits by having a very low prime volume and high oxygenation performance. The very low prime volume allows for the use of a single size of oxygenator for a much larger range of patient weights, not possible with oxygenators presently on the market having equivalent oxygenation capacity. Therefore, the two sizes of oxygenator shown herein are sufficient to cover a range of patients from neonatal to adults weighing in excess of 300 pounds (140 kg). More specifically, the neonatal/infant oxygenator 450 shown and described with respect to FIGS. 5 and 5a is designed for use in extracorporeal circuits for patients ranging from neonatals up to patients weighing about 44 pounds (20 kg). The adult oxygenator 150 in FIGS. 3 and 3a is designed for use in extracorporeal circuits for patients ranging in weight from about 44 pounds (20 kg) to about 308 pounds (140 kg).

A number of factors contribute to make the oxygenator of the present invention superior from those currently available. Some of these factors include the removal of the heat exchanger from incorporation in the oxygenator to the reservoir, the particular geometry of the oxygenator, and a hollow fiber architecture which is particularly well-suited to function within and complement the specific oxygenation chamber design. The advantages of removing the heat changer from the oxygenator have been described above. A detailed description of the particular geometry of the improved oxygenator follows.

Figure 7:
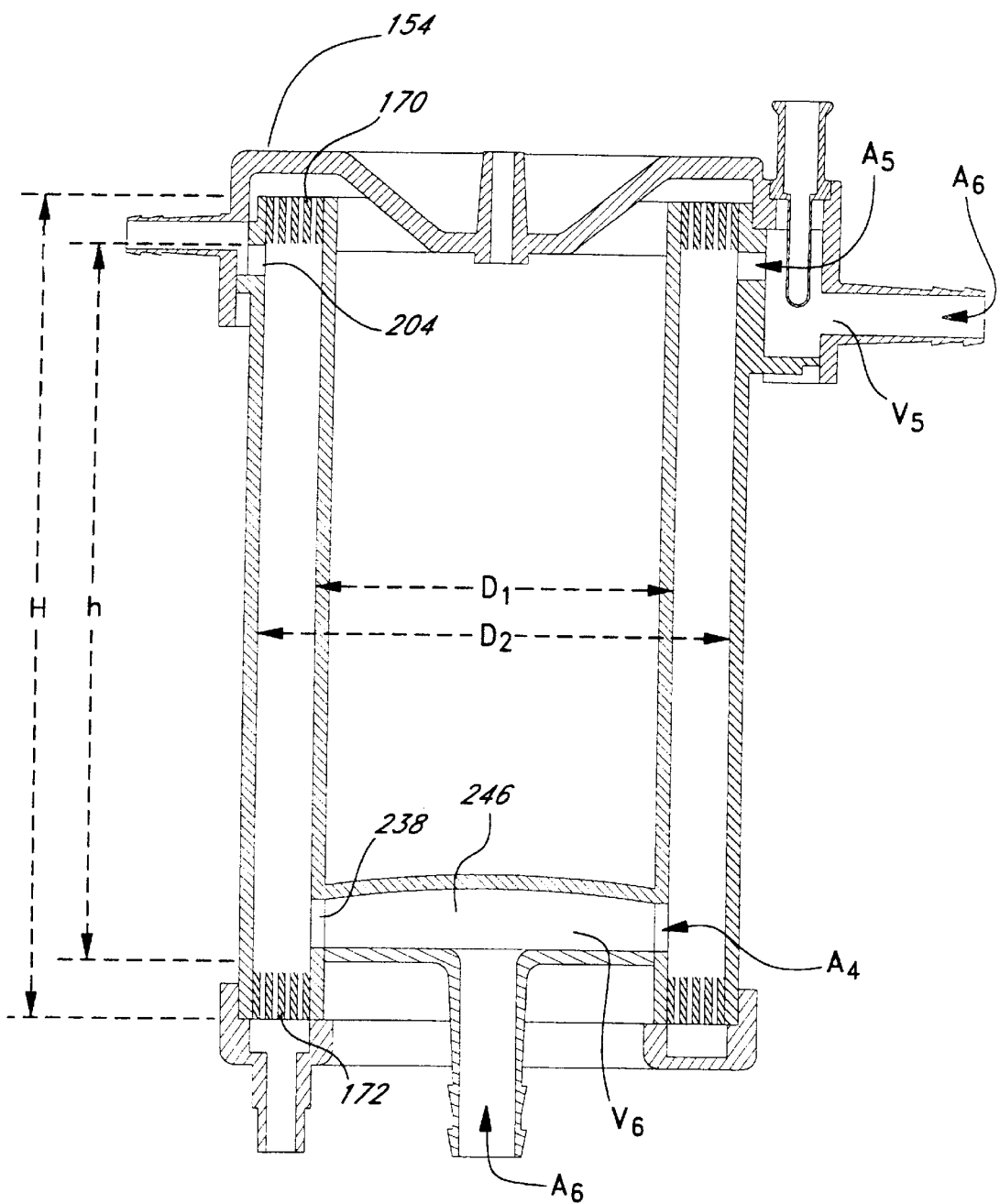
FIG. 7 is a cross-sectional view of the adult low prime volume oxygenator of FIG. 3 showing various key dimensions.

With reference to FIG. 7, the adult low prime oxygenator 150 previously described with reference to FIGS. 3 and 3a is shown with various key dimensions indicated. The oxygenation chamber 168 is defined between the outer diameter $D_1$ of the inner wall 166 and the inner diameter $D_2$ of the outer wall 164. H indicates the common length of both the outer wall 164 and inner wall 166, while the length between the two potting regions 170 and 172 is indicated as h. Therefore, the oxygenation chamber 168, 468 has a height h. A number of cross-sectional areas derived from the axial and radial dimensions, are defined as follows, with the first three being taken normal to the axis of the cylindrical walls:

$A_1$=the annular area of the oxygenation chamber $A_2$=the aggregate area within the hollow fibers $A_3$=the area of the blood flow within the oxygenation chamber 168 (i.e., the area outside of the hollow fibers)

$A_4$=the total area of the oxygenation chamber inlets 238

$A_5$=the total area of the oxygenation chamber outlets 204

$A_6$=the cross-sectional area of the blood inlet and outlet connectors $A_7$=the aggregate effective external surface area of the hollow fibers in the oxygenation chamber From the above dimensions, a number of volumes may be calculated as follows:

$V_1$=the volume between the inner and outer walls without the potting regions 170, 172

$V_2$=the volume between the inner and outer walls without the potting regions, and outside the hollow fibers $V_3$=the volume occupied by the aggregate fibers without the potting regions $V_4$=the volume occupied by the aggregate fibers between the potting regions $V_5$=the priming volume of the top cap 154

$V_6$=the priming volume of the blood distribution space 246

$v_1$=the volume between the inner and outer walls and the potting regions $v_2$=the volume between the inner and outer walls and the potting regions, and outside the hollow fibers (static priming volume)

A number of mathematical relations between these geometries may be stated:

$$A_1 = A_2 + A_3 = \Pi/4(D_2^2 - D_1^2)$$

$$V_1 = A_1 \times H = V_2 + V_3$$

$$v_1 = A_1 \times h = v_2 + V_4$$

The preferred relationships between the geometric parameters for the adult low prime oxygenator 150 described with respect to FIGS. 3 and 3a are as follows (it should be noted that the corresponding units can be found in Table II, and any necessary conversions are implicit in the RESULT column):

TABLE I

| CORRELATION | CALCULATION | RESULT |
|---|---|---|
| $D_2$ with $D_1$ | $(D_2^2 - D_1^2) \times \pi/4$ | $24 \leq A_1 \leq 28$ |
| $A_1$ with H | $A_1 \times H$ | $370 \leq V_1 \leq 410$ |
| $A_1$ with H | $H/A_1$ | $5 \leq H/A_1 \text{ (mm/cm}^2\text{)} \leq 6$ |
| $v_1$ with $V_4$ | $v_1 - V_4$ | $130 \leq v_2 \leq 180$ |
| $v_1$ with $V_4$ | $V_4/v_1$ | $0.5 \leq V_4/v_1 \leq 0.6$ |

It will also be understood that the preferred ranges given in Table I (and the other tables herein) are specific to the metric units used in the example, but are translatable to other units with appropriate calculations which would be apparent to those skilled in the art. For example, the first calculation of $A_1$ would have a different result if inches were the units; as in the following calculation with preferred dimensions:

$$D_1 = 85 \text{ mm} = 3.35 \text{ in}$$

$$D_2 = 62 \text{ mm} = 2.44 \text{ in}$$

$$A_1 = (D_2^2 - D_1^2) \times \pi/4 = 4.14 \text{ in}$$

Therefore, the ranges given above must be converted to appropriate units, but represent optimum geometrical relations which ensure a relatively high oxygen transfer rate and blood flow in an oxygenator with a low prime volume. One important parameter represented in Table I is the ratio of the volume of the aggregate fibers ($V_4$) to the volume between the inner and outer walls ($v_1$). That is, how much space does the fiber take up within the blood chamber, or, conversely, how much space is allowed for blood flow? This ratio ($V_4/v_1$) in relation to the absolute difference in the volumes ($v_1 - V_4$) is one reason for the enhanced performance of the present oxygenator.

The following table shows a range of exemplary values as well as a particularly preferred value of the above parameters for the adult low prime oxygenator 150.

TABLE II

| | ACTUAL | RANGE |
|---|---|---|
| $A_1$ | 26.9 cm² | 24–28 |
| $A_2$ | 15.5 cm² | 14–17 |
| $A_3$ | 11.3 cm² | 10–13 |
| $A_4$ | 8.4 cm² | 7–10 |
| $A_5$ | 9.5 cm² | 8–11 |
| $A_6$ | 0.7 cm² | 0.5–0.8 |
| $A_7$ | 2.0 m² | 1.9–2.0 |
| $D_1$ | 61.7 mm | 60–63 |
| $D_2$ | 85.0 mm | 83–87 |
| H | 145.0 mm | 143–147 |

TABLE II-continued

| | ACTUAL | RANGE |
|---|---|---|
| h | 125.0 mm | 110–130 |
| $V_1$ | 389.3 ml | 370–410 |
| $v_1$ | 335.6 ml | 320–360 |
| $V_2$ | 156.4 ml | 140–180 |
| $v_2$ | 149.3 ml | 130–180 |
| $V_3$ | 232.9 ml | 210–250 |
| $V_4$ | 186.3 ml | 170–210 |
| $V_5$ | 8.1 ml | 6–10 |
| $V_6$ | 6.5 ml | 5–9 |

Similar considerations for the adult low prime oxygenator are shared by the neonatal/infant low prime oxygenator 450 described with respect to FIGS. 5 and 5a. The preferred relationships between the geometric parameters are modified for this smaller size oxygenator as follows (again, the corresponding units can be found in Table IV, and any necessary conversions are implicit in the RESULT column):

TABLE III

| CORRELATION | CALCULATION | RESULT |
|---|---|---|
| $D_2$ with $D_1$ | $(D_2^2 - D_1^2) \times \Pi/4$ | $24 \leq A_1 \leq 28$ |
| $A_1$ with H | $A_1 \times H$ | $200 \leq V_1 \leq 240$ |
| $A_1$ with H | $H/A_1$ | $2.5 \leq H/A_1 \text{ (mm/cm}^2\text{)} \leq 3.5$ |
| $v_1$ with $V_4$ | $v_1 - V_4$ | $56 \leq v_2 \leq 80$ |
| $v_1$ with $V_4$ | $V_4/v_1$ | $0.5 \leq V_4/v_1 \leq 0.6$ |

The following table shows a range of exemplary values and a particularly preferred value for the various parameters in the neonatal/infant low prime oxygenator 450.

TABLE IV

| | ACTUAL | RANGE |
|---|---|---|
| $A_1$ | 26.9 cm² | 24–28 |
| $A_2$ | 15.5 cm² | 14–17 |
| $A_3$ | 11.3 cm² | 10–13 |
| $A_4$ | 4.2 cm² | 3–6 |
| $A_5$ | 4.1 cm² | 3–6 |
| $A_6$ | 0.3 cm² | 0.2–0.4 |
| $A_7$ | 1.0 m² | 0.9–1.0 |
| $D_1$ | 61.7 mm | 60–63 |
| $D_2$ | 85.0 mm | 83–87 |
| H | 81.0 mm | 79–83 |
| h | 60.0 mm | 58–62 |
| $V_1$ | 217.5 ml | 200–240 |
| $v_1$ | 161.1 ml | 140–180 |
| $V_2$ | 87.5 ml | 70–100 |
| $v_2$ | 70.4 ml | 56–80 |
| $V_3$ | 129.9 ml | 120–140 |
| $V_4$ | 90.6 ml | 80–100 |
| $V_5$ | 8.1 ml | 6–10 |
| $V_6$ | 6.5 ml | 5–9 |

A comparison of the present adult oxygenator 150 with oxygenators of similar capacity is given in the following chart:

TABLE V

PERFORMANCE COMPARISON OF ADULT MEMBRANE OXYGENATORS

| MFG | MODEL | HOLLOW FIBER EFFECTIVE SURFACE AREA ($m^2$) | ARTERIAL $O_2$ PARTIAL PRESSURE (mmHg) (at 7 lpm blood flow) | $O_2$ XFER ≥ 50 ml/min/lpm (at 7 lpm blood flow) | $CO_2$ XFER ≥ 42 ml/min/lpm (at 7 lpm blood flow) | PRESSURE DROP (mmHg) (at 7 lpm blood flow) | PRIME VOLUME (ml) | H.E. PERFORMANCE FACTOR |
|---|---|---|---|---|---|---|---|---|
| MACCHI | Present Invention | 0.7 | 248 | 57.5 | 55 | 137 | 170 | 0.48 |
| BENTLEY | SPIRAL GOLD | 1.9 | 209 | 57.7 | 52 | 69 | 265 | 0.48 |
| SARNS | SARNS TURBO | 1.9 | 310 | 57.7 | 58 | 270 | 270 | 0.65 |
| MEDTRONIC | MAXIMA PLUS | 2.3 | 222 | 56.9 | 54 | 116 | 480 | 0.44 |
| AVECOR | AFFINITY | 2.5 | 235 | 57.5 | 54 | 100 | 270 | 0.48 |
| TERUMO | CAPIOX SX | 1.8 | 112 | 55.1 | 45 | 202 | 270 | 0.52 |
| COBE | OPTIMA | 1.7 | 131 | 56.9 | 47 | 187 | 260 | 0.56 |
| BARD | HF 5700 | 3.7 | 304 | 57.9 | 57 | 187 | 560 | 0.48 |
| SORIN | MONOLYTH | 2.2 | 155 | 56.9 | 48 | 89 | 290 | 0.52 |
| MACCHI | OXIM II-34 PLUS | 3.2 | 350 | 57.6 | 56 | 105 | 490 | 0.46 |
| MACCHI | OXIM II-34 | 2.2 | 212 | 58.1 | 57 | 167 | 530 | 0.46 |

From this chart it is readily apparent that the present adult oxygenator 150 provides a large advantage over the competition in one of the key aspects of a successful oxygenator, its priming volume. The low priming volume of 170 ml is nearly 100 ml less than the next smallest, and nearly 400 ml less than the largest in this group. In addition, the oxygenator 150 has the lowest effective aggregate hollow fiber surface area, and performs acceptably in all the other categories in comparison with the competition. The reduction in hollow fiber surface area translates into a lower cost for the oxygenator.

Importantly, the oxygenator 150 has an $O_2$ transfer rate of about 57.5 ml/min/lpm at a blood flow rate of about 7 lpm. This means that the oxygenator 150 transfers a volume of oxygen that more than one third of its blood prime volume in one minute, at a flow rate of 7 lpm (which is typical for adult patients). The ratio of the oxygen transfer rate (at the prescribed flow rate) to prime volume is about 0.34 (57.5/170) lpm/min. The nearest competitor has such a ratio of only about 0.22 (56.9/260) lpm/min.

A comparison chart similar to the one given above for the neonatal/infant oxygenator 450 is provided below.

TABLE VI

PERFORMANCE COMPARISON OF NEONATE/INFANT MEMBRANE OXYGENATORS

| MFG | MODEL | PATIENT WEIGHT | MAXIMUM BLOOD FLOW (lpm) | PRIME VOLUME (ml) | PRESSURE DROP (mmHg) (at 1 lpm blood flow) | PRIME VOLUME (ml) (at 1 lpm blood flow) | HOLLOW FIBER EFFECTIVE SURFACE AREA ($m^2$) |
|---|---|---|---|---|---|---|---|
| MACCHI | Present Invention | Neonate/Infant | 2.0 | 60 | 27 | 0.75 | 1.0 |
| BENTLEY | Baby Spiral | Infant | 2.0 | 115 | 4 | 0.78 | N/A |
| MEDTRONIC | Minimax | Infant | 1.5 | 140 | 62 | 0.6 | 0.6 |
| DIDECO | Liliput | Neonate | 0.8 | 60 | 45 (at 0.8 lpm blood flow) | 0.82 (at 0.8 lpm blood flow) | 0.34 |
| DIDECO | 702 | Infant | 2.5 | 150 | 40 | 0.72 | 0.62 |
| TERUMO | Capiox 308 | Neonate | 0.8 | 80 | 75 (at 0.8 lpm blood flow) | 0.82 (at 0.8 lpm blood flow) | 0.8 |
| POLYSTAN | Safe Micro | Neonate | 0.8 | 52 | 0.87 (at 0.8 lpm blood flow) | 0.87 (at 0.8 lpm blood flow) | 0.33 |

Again, the priming volume of the neonatal/infant oxygenator 450 is the lowest in its class, along with the Dideco Liliput, which also has a priming volume of 60 ml. The Dideco oxygenator, however, has a maximum blood flow of only 0.8 lpm, and is thus only suitable for use with neonatal patients. In contrast, the present oxygenator 450 has a blood flow of up to 2.0 lpm, and is a suitable for use with both neonatal and infant patients. Importantly, the oxygenator 450 has an $O_2$ transfer rate of about 62.5 ml/min/lpm at a blood flow rate of about 2 lpm. This means that the oxygenator 450 transfers a volume of oxygen of the same magnitude as its blood prime volume in one minute, at a flow rate of 2 lpm (which is typical for infant patients). The ratio of the oxygen transfer rate (at the prescribed flow rate) to prime volume is about 1.04 lpm/min. Furthermore, the neonatal/infant oxygenator 450 is comparable in all other categories, although it has a slightly larger hollow fiber effective surface area, and thus requires more fibers, which is a small price to pay for the reduction in prime volume.

Heat Exchanger Advantages

In addition to providing a low prime volume oxygenator, the present invention realizes several advantages by moving the heat exchange function from the oxygenator to the reservoir. First, the heat exchanger is highly efficient.

Tables V and VI also illustrate the performance factor of the present heat exchanger positioned in the reservoir in comparison to the performance factor of the heat exchangers in prior art heat exchangers. The performance factor is a measure of the temperature change of the respective fluids passing through the heat exchanger (here, typically blood and water), and is calculated as follows:

$$P.F.=(T_{b,out}-T_{b,in})/(T_{w,in}-T_{b,in})$$

where:

$T_{b,in}$=Inlet temperature of the blood $T_{b,out}$=Outlet temperature of the blood $T_{w,in}$=Inlet temperature of the water As can be seen, the performance factor of the heat exchanger of the present invention is comparable to those of the prior art. This results from the specific arrangement of the heat exchanger within the reservoir. Although there have been reservoirs in the prior art incorporating heat exchange coils, they have been what may be termed flooded chamber reservoirs with relatively inefficient heat exchange capacities. With flooded chamber reservoirs, the performance of the heat exchanger is a function of the blood level therein. The present heat exchange/reservoirs shown and described above utilize a separate heat exchange chamber within the reservoir chamber to provide a single pass of blood across the heat exchange coils. That is, blood enters the reservoir chamber at an upper end and is guided through the annular heat exchange chamber and across all of the coils. Therefore, heat transfer takes place in a fairly confined region and a maximum volume of blood is in and around the heat exchange coils at all times, so that the heat transfer therebetween is made more efficient. Perhaps more importantly, the performance of the heat exchanger is not a function of the blood level in the reservoir.

One disadvantage from locating the heat exchanger in the oxygenation chamber, in a so-called closed system, is that the blood is submitted to certain additional stress. By locating the heat exchanger in the reservoir, as in the present invention, mechanical stress on the blood is reduced. That is, the blood passes through the heat exchanger by gravity (or under a slight vacuum) in a natural drainage progression rather than being forced past heat exchange tubes or fins with a fluid pressure generated by a pump. Of course, the blood exiting the reservoir is then impelled through the oxygenator and back to the patient using a pump, but the separation of the heat exchange and pressure elevation stages in the extracorporeal system helps reduce damage to the blood. In other words, the blood is not subjected to mechanical stresses within the heat exchange chamber.

Finally, the arrangement of the heat exchanger within the reservoir further reduces the prime volume of the entire extracorporeal circuit. In contrast to flooded chamber reservoirs, blood enters the reservoir chamber at an upper end and falls by gravity through the annular heat exchange chamber and across the coils before being filtered and flowing into the lower portion of reservoir chamber. Thus, previously unused volume within the reservoir chamber is now utilized by the heat exchanger.

It is understood that the examples and embodiments described herein and shown in the drawings represent only the presently preferred embodiments of the invention, and are not intended to exhaustively describe in detail all possible embodiments in which the invention may take physical form. Indeed, various modifications and additions may be made to such embodiments without departing from the spirit and scope of the invention.

What is claimed is:

1. A combined heat exchanger/blood reservoir, comprising:

a housing topped by a lid together defining a reservoir chamber within;

a venous blood inlet in the lid;

a heat exchanger within the chamber including a plurality of heat exchange elements;

an annular heat exchange chamber enclosing the heat exchange elements, the annular heat exchange chamber defined by concentric inner and outer guides that lie closely adjacent the heat exchange elements and extend downward from a location at an upper portion of the reservoir chamber, the heat exchange chamber having an upper inlet open to the venous blood inlet must flow through the heat exchange chamber before reaching the reservoir chamber; and a blood outlet in a lower portion of the reservoir chamber.

2. The apparatus of claim 1, wherein the housing further comprises a floor and the distance from the floor to the lid defines the height of the reservoir chamber, and wherein the guides forming the heat exchange chamber extend downward to a position that is approximately ¼ the height of the reservoir chamber.

3. The apparatus of claim 2, further including a filter member positioned between the heat exchange chamber outlet and the reservoir chamber outlet, the filter member surrounding the heat exchange chamber and having an upper edge above the elevation above the heat exchange chamber outlet.

4. The apparatus of claim 3, wherein the filter member comprises a non-woven filter.

5. The apparatus of claim 1, wherein the guides defining the heat exchange chamber are concentric tubular members so that the heat exchange chamber is annular.

6. The apparatus of claim 5, wherein the heat exchange elements comprise hollow tubes coiled within the annular heat exchange chamber.

7. The apparatus of claim 1, further including a defoaming element positioned within the lid between the venous blood inlet and the heat exchange chamber inlet, and at least one cardiotomy fluid inlet in the lid positioned so that cardiotomy fluid and venous blood both pass through the defoaming element and into the heat exchange chamber inlet.

8. The apparatus of claim 1, further including a first temperature probe mounted in the lid to sense the temperature of the inlet venous blood, and a second temperature probe mounted in the housing to sense the temperature of the blood in the reservoir chamber outlet.

* * * * *

UNITED STATES PATENT AND TRADEMARK OFFICE
CERTIFICATE OF CORRECTION

PATENT NO. : 6,613,281 B2
DATED : September 2, 2003
INVENTOR(S) : Filho et al.

It is certified that error appears in the above-identified patent and that said Letters Patent is hereby corrected as shown below:

<u>Column 10,</u>
Line 9, after "turret" please add -- 364 --

<u>Column 20,</u>
Line 29, after "inlet" please add -- and a lower outlet open to the reservoir chamber so that blood from the venous blood inlet --

Signed and Sealed this

Twenty-ninth Day of June, 2004

JON W. DUDAS
*Acting Director of the United States Patent and Trademark Office*